(12) United States Patent
Wu et al.

(10) Patent No.: US 11,970,570 B2
(45) Date of Patent: *Apr. 30, 2024

(54) BROMINATED FLAME RETARDANT AND ITS APPLICATION IN POLYURETHANE FOAMS

(71) Applicant: Albemarle Corporation, Charlotte, NC (US)

(72) Inventors: Tse-Chong Wu, Baton Rouge, LA (US); Augusto Caesar Ibay, Baton Rouge, LA (US); Joseph Morgan O'Day, Waxhaw, NC (US)

(73) Assignee: Albemarle Corporation, Charlotte, NC (US)

( * ) Notice: Subject to any disclaimer, the term of this patent is extended or adjusted under 35 U.S.C. 154(b) by 314 days.

This patent is subject to a terminal disclaimer.

(21) Appl. No.: 16/625,107

(22) PCT Filed: Jun. 26, 2018

(86) PCT No.: PCT/US2018/039578
§ 371 (c)(1),
(2) Date: Dec. 20, 2019

(87) PCT Pub. No.: WO2019/067047
PCT Pub. Date: Apr. 4, 2019

(65) Prior Publication Data
US 2020/0140639 A1    May 7, 2020

Related U.S. Application Data

(60) Provisional application No. 62/564,532, filed on Sep. 28, 2017.

(51) Int. Cl.
| | | |
|---|---|---|
| C08G 18/76 | (2006.01) | |
| C07C 17/02 | (2006.01) | |
| C07C 29/62 | (2006.01) | |
| C08G 18/00 | (2006.01) | |
| C08G 18/08 | (2006.01) | |
| C08G 18/18 | (2006.01) | |
| C08G 18/40 | (2006.01) | |
| C08G 18/42 | (2006.01) | |
| C08G 18/48 | (2006.01) | |
| C08J 9/00 | (2006.01) | |
| C08J 9/12 | (2006.01) | |
| C08J 9/14 | (2006.01) | |
| C08K 5/05 | (2006.01) | |

(52) U.S. Cl.
CPC .......... *C08G 18/7664* (2013.01); *C07C 17/02* (2013.01); *C07C 29/62* (2013.01); *C08G 18/00* (2013.01); *C08G 18/0847* (2013.01); *C08G 18/1808* (2013.01); *C08G 18/1825* (2013.01); *C08G 18/4018* (2013.01); *C08G 18/4208* (2013.01); *C08G 18/4829* (2013.01); *C08G 18/4854* (2013.01); *C08G 18/4858* (2013.01); *C08J 9/0023* (2013.01); *C08J 9/125* (2013.01); *C08J 9/148* (2013.01); *C08K 5/05* (2013.01); *C08G 2110/0008* (2021.01); *C08G 2110/0025* (2021.01); *C08G 2110/005* (2021.01); *C08J 2203/10* (2013.01); *C08J 2203/144* (2013.01); *C08J 2203/164* (2013.01); *C08J 2205/05* (2013.01); *C08J 2205/052* (2013.01); *C08J 2205/06* (2013.01); *C08J 2205/10* (2013.01); *C08J 2375/08* (2013.01)

(58) Field of Classification Search
CPC ....... C07C 17/02; C07C 29/62; C07C 33/423; C08G 18/00; C08G 18/0847; C08G 18/1808; C08G 18/1825; C08G 18/2885; C08G 18/4018; C08G 18/42; C08G 18/4208; C08G 18/4829; C08G 18/4854; C08G 18/4858; C08G 18/7664; C08G 2110/0008; C08G 2110/0025; C08G 2110/005; C08G 2110/0083; C08J 9/0019; C08J 9/0023; C08J 9/125; C08J 9/144; C08J 9/148; C08J 2203/10; C08J 2203/144; C08J 2203/164; C08J 2205/05; C08J 2205/052; C08J 2205/06; C08J 2205/10; C08J 2375/08; C08K 5/05
See application file for complete search history.

(56) References Cited

U.S. PATENT DOCUMENTS

| | | |
|---|---|---|
| 3,283,013 A | 11/1966 | Rimmer |
| 3,334,032 A | 8/1967 | Rumson |
| 3,467,607 A | 9/1969 | Kuryla et al. |
| 3,487,040 A | 12/1969 | Jolles |

(Continued)

FOREIGN PATENT DOCUMENTS

| | | |
|---|---|---|
| CA | 2182714 A1 | 2/1997 |
| CN | 1179440 A | 4/1998 |

(Continued)

OTHER PUBLICATIONS

Gharibyan, H. A., et al., "Hydroalumination-Bromination of Acetylenic α-Alcohols", Hayastani Kimiakan Handes, 2009, vol. 62, pp. 369-377.

(Continued)

*Primary Examiner* — John M Cooney
(74) *Attorney, Agent, or Firm* — KDW Firm PLLC

(57) ABSTRACT

This invention provides polyurethane foams containing a brominated flame retardant. Also provided are formulations and methods for preparing polyurethane foams containing a brominated flame retardant.

16 Claims, No Drawings

(56) References Cited

U.S. PATENT DOCUMENTS

| | | | |
|---|---|---|---|
| 3,542,740 | A | 11/1970 | Pumpelly et al. |
| 3,637,813 | A | 1/1972 | D'Alelio |
| 3,780,144 | A | 12/1973 | D'Alelio |
| 3,932,181 | A | 1/1976 | Ray-Chaudhuri et al. |
| 3,933,690 | A | 1/1976 | D'Alelio et al. |
| 3,950,392 | A | 4/1976 | D'Alelio |
| 3,993,690 | A | 11/1976 | Suvorov et al. |
| 4,002,580 | A | 1/1977 | Russo |
| 4,559,366 | A | 12/1985 | Hostettler |
| 4,697,029 | A | 9/1987 | Collin et al. |
| 4,745,133 | A | 5/1988 | Grinbergs et al. |
| 4,898,981 | A | 2/1990 | Falk et al. |
| 6,518,324 | B1 | 2/2003 | Kresta et al. |
| 7,572,837 | B2 | 8/2009 | Kometani et al. |
| 7,671,105 | B2 | 3/2010 | Krupa et al. |
| 7,862,749 | B2 | 1/2011 | Sjerps |
| 8,877,825 | B2 | 11/2014 | Komentani et al. |
| 9,434,884 | B2 | 9/2016 | Lubnin et al. |
| 2002/0107422 | A1 | 8/2002 | Doi et al. |
| 2003/0092786 | A1 | 5/2003 | Brassat et al. |
| 2003/0153656 | A1 | 8/2003 | Sjerps |
| 2006/0135636 | A1 | 6/2006 | Zhu et al. |
| 2009/0149561 | A1 | 6/2009 | Worku et al. |
| 2012/0248371 | A1 | 10/2012 | Ross et al. |
| 2013/0217286 | A1 | 8/2013 | Lubnin et al. |
| 2014/0005288 | A1 | 1/2014 | Chen et al. |
| 2014/0171525 | A1 | 6/2014 | Yu et al. |
| 2014/0220333 | A1 | 8/2014 | Bogdan et al. |
| 2015/0025164 | A1 | 1/2015 | Golini et al. |
| 2016/0251491 | A1 | 9/2016 | Okada et al. |
| 2017/0247496 | A1 | 8/2017 | Wang et al. |
| 2018/0022885 | A1* | 1/2018 | Younes .............. C08G 18/4018 427/243 |

FOREIGN PATENT DOCUMENTS

| | | |
|---|---|---|
| CN | 10 1092535 A | 12/2007 |
| CN | 102391766 A | 3/2012 |
| CN | 10 2964562 A | 3/2013 |
| CN | 10 3665915 A | 3/2014 |
| CN | 10 6380600 A | 2/2016 |
| CN | 10 5860505 A | 8/2016 |
| CN | 105837781 A | 8/2016 |
| CN | 10 6280451 A | 1/2017 |
| CN | 10 6317873 A | 1/2017 |
| DE | 2344254 A1 | 3/1974 |
| EP | 0 758 068 B1 | 12/1999 |
| EP | 1 756 224 B1 | 10/2007 |
| GB | 2 019 858 A | 11/1979 |
| IN | 10 3102844 A | 5/2013 |
| JP | H09-039104 A | 2/1997 |
| PL | 198605 B1 | 7/2008 |
| TW | 200300145 A | 5/2003 |
| TW | 200815489 A | 4/2008 |
| TW | 200936664 A | 9/2009 |
| TW | 201117877 A | 6/2011 |
| WO | 2015/041552 A2 | 3/2015 |
| WO | 2019/005837 A1 | 1/2019 |

OTHER PUBLICATIONS

Kodomari, M., et al., "Stereoselective Bromination of Acetylenes with Bromine in the Presence of Graphite", Bull. Chem. Soc. Jpn., 1989, vol. 62, pp. 4053-4054.

Schuh, Kerstin, et al., "A Domino Copper-Catalyzed C—N and C—O Cross-Coupling for the Conversion of Primary Amides into Oxazoles", Synthesis, 2007, pp. 2297-2306.

ICL Industrial Products. (2012). "Fire Safety in Construction and Building with ICL-IP Solutions", product brochure, 6 pages.

Sigma-Aldrich. "2,3-Dibromo-1-propanol", product information, www.sigmaaldrich.com/catalog/product/aldrich/d43050?lang=en&region=US, website visited Dec. 15, 2020, 3 pages.

LanXess, Energizing Chemistry, PHT4-DIOL Lv Reactive Halogenated Flame Retardant Data Sheet, May 2016, 3 pages.

European Chemicals Agency (ECHA). "Reaction products of tetrabromophthalic anhydride with 2,2'-oxydiethanol and methyloxirane." Registration Dossier. https://echa.europa.eu/registration-dossier/-/registered-dossier/26127. Viewed on Mar. 9, 2022.

* cited by examiner

BROMINATED FLAME RETARDANT AND ITS APPLICATION IN POLYURETHANE FOAMS

REFERENCE TO RELATED APPLICATIONS

This application is the National Stage of International Patent Appln. No. PCT/US2018/039578 filed on Jun. 26, 2018, which in turn claims the benefit of U.S. Provisional Patent Appln. No. 62/564,532, filed on Sep. 28, 2017, the disclosures of which are incorporated herein by reference.

TECHNICAL FIELD

This invention relates to a brominated short-chain alcohol useful as a flame retardant in flexible and rigid polyurethane foams.

BACKGROUND

Fire resistance is an important property of polyurethane foams. Various compounds or mixtures thereof have been used effectively to meet applicable fire safety standards. Tris(1-chloro-2-propyl) phosphate (TCPP) is a flame retardant widely used in polyurethane foams. However, TCPP is a non-reactive compound in polyurethane foam formation and can thus leach or migrate from the foams. This results in health and environmental concerns.

A brominated isocyanate-reactive compound that has been disclosed as a flame retardant is 2,3-dibromobutene-1,4-diol (e.g., U.S. Pat. No. 4,002,580). However, 2,3-dibromobutene-1,4-diol (DBBD) is a solid with a high melting point and requires additional steps to pre-dissolve for it to be useful in polyurethane foam applications.

Thus, it would be desirable to have a flame retardant that is a liquid at processing conditions and has low viscosity to allow ease of processing (mixing and pumping). In addition to effectiveness as flame retardants, it is desired to provide compounds that are compatible with polyurethane foam manufacturing processes, and do not migrate out of the polyurethane foam over time, lessening the health and environmental impacts.

SUMMARY OF THE INVENTION

This invention provides formulations and processes for producing flame retardant polyurethane foams. More specifically, this invention provides an isocyanate-reactive brominated flame retardant compound that is useful in polyurethane forms. In particular, the invention relates to the application of 2,3-dibromo-2-propen-1-ol (2,3-dibromoallyl alcohol or DBAA) in polyurethane foams, including open-cell spray foams, closed-cell spray foams, rigid panel foams, and flexible foams.

An embodiment of this invention is a polyurethane foam formed from ingredients comprising DBAA.

Also provided are formulations that can be used to make flame retardant polyurethane foams.

Other embodiments of this invention include processes for forming polyurethane foams.

FURTHER DETAILED DESCRIPTION OF THE INVENTION

As used throughout this document, the phrase "reactive brominated flame retardant" has equivalent meaning to "isocyanate-reactive brominated flame retardant."

Polyurethane foams are typically produced by contacting two main liquid components, viz., polyisocyanates (A side) and polyols (B side). It is desirable for the B side (here, the formulation of the invention), which contains all of the components other than the polyisocyanates, to be in the form of a liquid. As used herein, the term "liquid" means that the formulation is in the liquid state at the conditions at which the B side formulation is used. For more information regarding the formation of polyurethane foams, see for example U.S. Pat. Nos. 3,954,684; 4,209,609; 5,356,943; 5,563,180; and 6,121,338.

The present invention relates to polyurethane foams flame retarded with dibromoallyl alcohol (DBAA). These foams are formed from formulations comprising DBAA, at least one polyol, at least one blowing agent, at least one catalyst, and at least one surfactant, which formulations are contacted with a polyisocyanate.

An isocyanate-reactive brominated flame retardant contains at least one functional group which is available for, and capable of, reacting with another polyurethane-forming component during polyurethane formation so that the resultant polyurethane contains the reactive brominated flame retardant in chemically-bound form. It is believed that the functional groups of the reactive brominated flame retardant react with isocyanate groups during the preparation of polyurethane foam; usually, the functional (reactive) groups in the reactive brominated flame retardants are hydroxyl groups.

The isocyanate-reactive brominated flame retardant used in the practice of this invention, 2,3-dibromo-prop-2-en-1-ol, a known molecule (also referred to herein as dibromoallyl alcohol or DBAA), which has CAS® registry number 7228-11-7 (Chemical Abstracts Service). DBAA is not commercially available, but synthesis of DBAA from propargyl alcohol (2-propyn-1-ol) and elemental bromine ($Br_2$) at room temperature in a solvent is known. In the past, DBAA has been used as an intermediate to make phosphorus compounds (see U.S. Pat. No. 3,950,457).

DBAA can be used in forming both flexible polyurethane foams and rigid polyurethane foams. DBAA is a reactive component that becomes part of the polyurethane foam. This provides the advantage that DBAA does not migrate out of the foam. Another advantage is that DBAA has a high bromine content (74 wt %). Other flame retardants that can be included in the polyurethane foams with DBAA include a mixed ester of tetrabromophthalic anhydride with diethylene glycol and propylene glycol, tris(1-chloro-2-propyl) phosphate, or both tris(1-chloro-2-propyl)phosphate and a mixed ester of tetrabromophthalic anhydride with diethylene glycol and propylene glycol.

Formulations of the invention, which can be used as the B side in processes for forming polyurethane foams, comprise DBAA, a polyol, a blowing agent, a catalyst, and a surfactant.

In forming polyurethane foams of the invention, a flame retardant amount of DBAA is used. By a flame retardant amount is meant that amount of DBAA needed to obtain the desired level of flame retardancy. A flame retardant amount is typically in the range of about 1 wt % to about 25 wt %, preferably about 3 wt % to about 20 wt %, more preferably about 3 wt % to about 18%, based on the total weight of the formulation (B side components).

The polyol or polyols used in forming the polyurethane foams in the practice of this invention can be any polyol that is typically used to produce flexible polyurethane foams or rigid polyurethane foams. Often, mixtures of polyols are used, with the particular polyols selected for their effect on the properties of the polyurethane foam being formed.

When flexible polyurethane foam is being formed, the polyol usually is a polyol or mixture of polyols having hydroxyl numbers up to about 150 mg KOH/g, preferably in the range of about 5 mg KOH/g to about 150 mg KOH/g, more preferably about 10 to about 100 mg KOH/g, even more preferably about 20 mg KOH/g to about 75 mg KOH/g. When polymeric polyols are used, they typically have molecular weights in the range of about 2,000 to about 10,000, preferably about 3,000 to about 8,000.

When rigid polyurethane foam is being formed, the polyol usually is a polyol or mixture of polyols having hydroxyl numbers in the range of about 100 to about 850 mg KOH/g, preferably in the range of about 110 to about 600 mg KOH/g. When polymeric polyols are used, they typically have molecular weights in the range of about 250 to about 5000, often about 400 to about 3000.

Suitable polyols for forming polyurethane foams include polyether polyols, polyester polyols, aliphatic polyols, and polyoxyalkylene glycols. Mixtures of two or more polyols can be used. Preferred polyols for forming rigid polyurethane foams include polyester polyols.

Polyoxyalkylene glycols that can be used include polyoxyethylene glycol, polyoxypropylene glycol, and block and heteric polyoxyethylene-polyoxypropylene glycols.

The aliphatic polyols typically contain up to about 18 carbon atoms per molecule. Suitable aliphatic polyols include ethylene glycol, propylene glycol, the isomeric butylene glycols, diethylene glycol, 1,5-pentanediol, 1,6-hexanediol, triethylene glycol, glycerol, trimethylolethane, trimethylolpropane, 1,2,6-hexanetriol, pentaerythritol, tetraethylene glycol, dipentaerythritol, sorbitol, sucrose, and alpha-methylglycoside.

Polyether polyols are produced by reacting one or more alkylene oxides having 2 to about 8 carbons in the alkylene radical with an initiator molecule containing two or more hydroxyl groups. Suitable polyether polyols include sucrose/glycerine polyether polyol; sucrose polyether polyol based on glycerine, propylene oxide and ethylene oxide; glycerin-initiated polyether polyols, e.g., glycerine/propylene oxide polyether polyol; and mannich-based polyether polyols.

Polyester polyols are produced by polymerizing polycarboxylic acids or their derivatives, for example their acid chlorides or anhydrides, with a polyol. Suitable polyester polyols include aromatic polyester polyols and diethylene glycol-phthalic anhydride polyester polyol.

For forming both flexible and rigid polyurethane foams, the amount of polyol typically ranges from about 40 wt % to about 80 wt %, and often from about 50 wt % to about 70 wt %, based on the total weight of the B side components (formulation). These amounts refer to the total amount of polyol in the formulation, when there is more than one polyol present.

Blowing agents that can be used in this invention for forming flexible and rigid polyurethane foams include water, volatile hydrocarbons, hydrocarbons such as n-pentane, isopentane, cyclopentane; halocarbons (fully halogenated chlorofluorocarbons), in particular trichlorofluoromethane (CFC-11); and halohydrocarbons (hydrogen-containing chlorofluorocarbons, or HCFC's) such as 1,1-dichloro-1-fluoroethane (HCFC-141b), 1-chloro-1,1-difluoroethane (HCFC-142b), chlorodifluoromethane (HCFC-22). Mixtures of any two or more blowing agents can be used. In some instances, DBAA permits formulations in which water is the only blowing agent.

Other suitable blowing agents in the practice of this invention when forming flexible polyurethane foams include dichloromethane (methylene chloride) and acetone. Preferred blowing agents for flexible polyurethane foams include water. The amount of blowing agent for forming flexible foams may range from about 0.5 wt % to about 20 wt %, preferably about 2.5 wt % to about 15 wt %, based on the total weight of the B side components (formulation).

For forming rigid polyurethane foams, blowing agents which can be used in the practice of this invention include partially fluorinated hydrocarbons (HFC's). Suitable blowing agents for rigid foams include trans-1-chloro-3,3,3-trifluoropropene (HFO-1233zd(E)), 1,1,1,3,3-pentafluoropropane (HFC-245fa), 1,1,1,2-tetrafluoroethane (HFC-134a), 1,1,1,3,3,3-hexafluoropropane (HFC-236fa), 1,1,2,3,3,3-hexafluoropropane (HFC-236ea), 1,1,1,4,4,4-hexafluorobutane (HFC-356mffm), and 1,2-bis(trifluoromethyl)ethene; and hydrocarbons such as n-pentane, isopentane, and cyclopentane. Mixtures of any two or more blowing agents can be used.

Preferred blowing agents when forming rigid foams include water, 1,1,1,3,3-pentafluoropropane, trans-1-chloro-3,3,3-trifluoropropene, 1,2-bis(trifluoromethyl)ethene, and mixtures of water with 1,1,1,3,3-pentafluoropropane, trans-1-chloro-3,3,3-trifluoropropene, or 1,2-bis(trifluoromethyl)ethene. In some instances, 2,3-dibromoallyl alcohol permits formulations in which water is the only blowing agent. The amount of blowing agent for forming rigid foams may range from about 0.5 wt % to about 20 wt %, preferably about 2.5 wt % to about 15 wt %, based on the total weight of the B side components.

Various types of catalysts can be used in the practice of this invention when forming either flexible or rigid polyurethane foams, including tertiary amines, tin catalysts, typically an organic tin compound, bismuth catalysts, other organometallic catalysts, and potassium salts of organic carboxylic acids. Mixtures of catalysts of the same type and/or different types can be used in the practice of this invention.

In the amine catalysts, the groups on the amine are preferably alkyl groups; more preferably, the groups are oxygen-containing groups such as etheric or saturated alcoholic groups. Suitable amine catalysts include dimethylethyl amine, triethylenediamine, dimethylethylamine, dimethylcyclohexylamine, dimethylbenzylamine, tetramethyldipropylenetriamine, pentamethyldiethylenetriamine, tris(dimethylaminopropyl)-hydrotriazine, 1-methyl-4-(2-dimethylaminoethyl)piperazine, 1,4-diaza(2,2,2)bicyclooctane, 3-methoxy-N,N-dimethylpropylamine, N-methylmorpholine, N-ethylmorpholine, N-cocomorpholine, bis(dimethylaminoethyl) ether, and ethanol amine catalysts, such as dimethylethanolamine, 2-(2-dimethylaminoethoxy)ethanol, and N,N,N'-trimethylaminoethyl-ethanol amine. For flexible foams, preferred catalysts include 2-(2-dimethylaminoethoxy)ethanol. For rigid polyurethane foam, the amine catalyst is preferably a tertiary amine.

Types of tin compounds that can be used as catalysts include dialkyl(dialkylthio) stannanes, stannous(II) salts of organic carboxylic acids, and dialkyltin(IV) salts of carboxylic acids. Suitable tin catalysts in the practice of this invention include dibutylbis(dodecylthio) stannane, stannous(II) octoate, stannous(II) acetate, dibutyltin dilaurate, and dioctyltin diacetate.

Still another type of catalyst is one or more potassium salts of organic carboxylic acids. Suitable potassium salts include potassium acetate and potassium octoate.

The catalysts are usually used in a total amount of about 0.25 wt % to about 10 wt %, preferably about 1 wt % to about 8 wt %, based on the total weight of the formulation (B side components) for both the flexible and rigid polyurethane foams. These amounts refer to the total amount of catalyst in the formulation, when there is more than one catalyst present.

A surfactant is often needed for production of polyurethane foams, and surfactants are normally used when forming both flexible and rigid polyurethane foams.

For both flexible and rigid polyurethane foams, suitable silicone-based surfactants include silicone glycols, silicone glycol copolymers, polyether modified polysiloxanes, polyether modified dimethylpolysiloxanes such as a polyether polydimethylsiloxane copolymer, polysiloxane polyoxoalkylene copolymers, polysiloxane polyoxoalkylene copolymers, polysiloxane copolymers, and the like. Silicone-based surfactants are a preferred type of surfactant for forming both flexible and rigid polyurethane foams. Polyether modified dimethylpolysiloxanes and polysiloxane copolymers are preferred silicone-based surfactants.

Cell openers, typically polyalkylene oxides, are a preferred type of surfactant for flexible foams. Suitable polyalkylene oxide cell openers in the practice of this invention include polyethylene glycol monoallyl ether, polyethylene glycol allyl methyl diether, polyethylene glycol monoallyl ether acetate, polyethylene glycol monomethyl ether, polyethylene glycol glycerol ether, polyethylene-polypropylene glycol monoallyl ether, polyethylene-polypropylene glycol monoallyl monomethyl diether, and polyethylene-polypropylene glycol allyl ether acetate.

Other surfactants that can be used when forming rigid polyurethane foams include emulsifiers such as sodium salts of castor oil sulfates or fatty acids; fatty acid salts with amines, e.g., diethylamine oleate and diethanolamine stearate; salts of sulfonic acids, e.g., alkali metal or ammonium salts of e.g., dodecylbenzenedisulfonic acid and ricinoleic acid; ethoxylated alkylphenols, ethoxylated fatty alcohols; ether amine quaternary ammonia compounds; 2-hydroxypropyltrimethylammonium formate; sodium hydroxy-nonylphenyl-N-methylglycinate (the sodium salt of N-((2-hydroxy-5-nonylphenyl)methyl)-N-methyl-glycine), and castor oil.

For forming both flexible and rigid polyurethane foams, the surfactants are usually used in amounts of about 0.1 wt % to about 5 wt %, preferably about 0.5 wt % to about 5 wt %, based on the total weight of the B side components (formulation). These amounts refer to the total amount of surfactant in the formulation, when there is more than one surfactant present.

One or more optional additives which can be included in the formulation of the invention when forming either a flexible or a rigid polyurethane foam include antioxidants, diluents, chain extenders or cross-linkers, synergists (preferably melamine), stabilizers, fungistats, pigments, dyes, fillers, antistatic agents, and plasticizers.

The components of the formulation can be combined in any order; preferably, the blowing agent is the last ingredient added. More preferably, DBAA is combined with the polyol(s), followed by the surfactant, catalyst, and any optional ingredients, followed by the blowing agent.

The isocyanates or polyisocyanates (A-side component) used in forming the polyurethane foams in the practice of this invention can be any isocyanate or polyisocyanate that can be used to produce flexible polyurethane foams or rigid polyurethane foams, as appropriate. When a polymeric polyisocyanate is used, it preferably has an isocyanate (NCO) content of about 25 wt % to about 50 wt %, preferably about 25 wt % to about 40 wt %.

When forming flexible polyurethane foams, the isocyanate generally has at least two isocyanate groups. The isocyanates can be aliphatic or aromatic. When forming rigid polyurethane foams, polyisocyanates are used, and the polyisocyanate can be aromatic or aliphatic. Suitable polyisocyanates for both flexible and rigid polyurethane foams in the practice of this invention include, but are not limited to, 1,4-tetramethylene diisocyanate, 1,5-pentamethylene diisocyanate, 2-methyl-1,5-pentamethylene diisocyanate, 1,6-hexamethylene diisocyanate (HMDI), 1,7-heptamethylene diisocyanate, 1,10-decamethylene diisocyanate, cyclohexylene diisocyanate, isophorone diisocyanate (IPDI), 4,4'-methylenedicyclohexyl diisocyanate (H12MDI), hexahydrotoluene diisocyanate and isomers thereof, 2,2,4-trimethylhexamethylene diisocyanate, 2,4,4-trimethylhexamethylene diisocyanate, 4,4'-methylenebis(cyclohexylisocyanate), phenylene diisocyanate, toluene diisocyanate (TDI), xylene diisocyanate, other alkylated benzene diisocyanates, toluene diisocyanate, 1,5-naphthalene diisocyanate, diphenylmethane diisocyanate (MDI, sometimes called methylene diisocyanate), 1-methoxyphenyl-2,4-diisocyanate, 4,4'-diphenylmethane diisocyanate, 2,4'-diphenylmethane diisocyanate, mixtures of 4,4'- and 2,4'-diphenylmethane diisocyanate, 4,4'-biphenylene diisocyanate, 3,3'-dimethoxy-4,4'-biphenyl diisocyanate, 3,3'-dimethyl-4,4'-biphenyl diisocyanate, 4,4',4"-triphenylmethane triisocyanate, toluene 2,4,6-triisocyanate, 4,4'-dimethyldiphenylmethane-2,2',5,5'-tetraisocyanate, polymeric polyisocyanates such as polymethylene polyphenylene polyisocyanate, and mixture of any two or more of the foregoing.

Polyisocyanates that can be used in forming both the flexible and rigid polyurethane foams of the present invention include those isocyanates commonly referred to as polymeric methylene diphenyl diisocyanate (MDI), polyisocyanate-based prepolymers, and mixtures thereof. Polymeric MDI contains varying amounts of isomeric diphenylmethane diisocyanates and three-ring, four-ring, and greater than four-ring oligomers. In general, any commercial polymeric MDI having an isocyanate content of about 25 wt % or more may be used. A preferred polymeric MDI has an isocyanate content of about 30 wt % or more. Other isocyanates may be present with the polymeric MDI in minor amounts, as long as the polyisocyanate mixture as whole remains liquid. Preferably, the polyisocyanate is a polymeric MDI.

The polyurethane foam compositions of this invention are formed from A side and B side components in which the A side is one or more isocyanates or polyisocyanates as described above, and the B side comprises a formulation of the invention. The polyurethane formation reaction generally occurs readily at room temperature; normally, the A side and the B side begin to react with each other as soon as they are in contact, and continue to react (cure), forming a polyurethane foam. Often, the mixture of the A side and B side is sprayed or cast to form a polyurethane foam.

In the processes of the invention for forming polyurethane foams, A) at least one isocyanate and/or polyisocyanate is contacted with B) a formulation formed from 2,3-dibromoallyl alcohol, at least one polyol, at least one blowing agent, at least one catalyst, and at least one surfactant, to form a mixture; and the mixture is allowed to cure to form a polyurethane foam.

The amount of isocyanates and/or polyisocyanate may be defined in terms of the Isocyanate Index.

$$\text{Isocyanate Index} = \frac{\text{Actual equivalent amount of isocyanate used}}{\text{Theoretical equivalent amount of reactive hydrogens}} \times 100$$

The theoretical equivalent amount of isocyanate is equal to one equivalent of isocyanate per one equivalent of reactive hydrogens from the B side. In the processes of this invention, Isocyanate Index values typically range from 80 to 200 or about 90 to about 150. Rigid polyurethane foams are usually formed by bringing together polyisocyanates with compounds having isocyanate-reactive hydrogen atoms (e.g., hydroxyl groups) in amounts such that the Isocyanate Index is in the range of about 85 to about 1000, preferably from about 95 to about 400, more preferably about 95 to about 200

To form polyurethane foams, the functionality (i.e., average number of hydroxyl groups per molecule), of the formulation (B side) which is typically provided by the polyol or mixture of polyols, is usually about 2 or more, preferably about 2 to about 8; more preferably about 3 or more, especially about 3 to about 8, more especially about 3 to about 7. As a monoalcohol, DBAA has a functionality of one (i.e., one hydroxyl group in the molecule), which is chain-terminating, so at least a portion of the polyols in the formulation have three or more hydroxyl groups per molecule to form polyurethane foams. DBAA is included in the calculation of the average functionality of the B side.

In the polyurethane foams, the 2,3-dibromoallyl alcohol is generally about 0.5 wt % to about 12.5 wt %, preferably about 1.5 wt % to about 10 wt %, more preferably about 1.5 wt % to about 9%, based on the total weight of the polyurethane foam. Polyols typically ranges from about 20 wt % to about 40 wt %, and often from about 25 wt % to about 35 wt %, based on the total weight of the polyurethane foam. Surfactants are present in amounts of about 0.05 wt % to about 2.5 wt %, preferably about 0.25 wt % to about 2.5 wt %, based on the total weight of the polyurethane foam. The catalysts are present in a total amount of about 0.125 wt % to about 5 wt %, preferably about 0.5 wt % to about 4 wt %, based on the total weight of the polyurethane foam. These amounts refer to the total amount of each type of ingredient in the foam, when there is more than one of that type of ingredient present.

The rigid polyurethane foams formed in this invention have a density range that varies with the end use application. For open-cell insulation foams, the density range is generally about 0.4 lb/ft$^3$ to about 1.2 lb/ft$^3$ (6.3 kg/m$^3$ to 18.9 kg/m$^3$). For closed-cell insulation foams, the density range is typically about 1.6 lb/ft$^3$ to about 3.5 lb/ft$^3$ (25.6 kg/m$^3$ to 56.1 kg/m$^3$). For molded architectural foams, the density range is usually about 4.0 lb/ft$^3$ to about 31 lb/ft$^3$ (64.0 kg/m$^3$ to 497 kg/m$^3$).

The flexible polyurethane foams formed in this invention have a density range of about 0.5 to about 1.0 lb/ft$^3$ (8 to 16 kg/m$^3$). Flexible polyurethane foams are typically used to form articles such as molded foams, slabstock foams, and may be used as cushioning material in furniture and automotive seating, in mattresses, as carpet backing, as hydrophilic foam in diapers, and as packaging foam.

The following examples are presented for purposes of illustration, and are not intended to impose limitations on the scope of this invention. All percentages in the following examples are by weight unless otherwise noted.

EXAMPLES—GENERAL

In the Examples, some of the substances used are referred to by their trade names. More specifically:

DBAA: 2,3-dibromoallyl alcohol
Saytex® RB-79: a mixed ester of tetrabromophthalic anhydride with diethylene glycol and propylene glycol (Albemarle Corporation).
TCPP: tris(1-chloro-2-propyl)phosphate.
DE: diethylene glycol monoethyl ether.
Voranol® 280: a polyether polyol with a functionality of about 7.0, a hydroxyl number of about 280, and an average molecular weight of about 1400; Voranol® 370: a sucrose/glycerine polyether polyol with a functionality of 7.0; Voranol® 490: a sucrose/glycerine polyether polyol with a functionality of 4.3 (all Voranol® materials are products of Dow Chemical Company).
Vorasurf® 504 is a non-silicone organic surfactant (Dow Chemical Company).
Terate® HT 5503: an aromatic polyester polyol with a hydroxyl number in the range of 225 to 245, a functionality of 2, and an equivalent weight of 239; Terate® HT 5349: an aromatic polyester polyol with a functionality of about 2.45, and a hydroxyl number of 295 to 315 (all Terate® materials are products of Invista Corporation).
Stepanpol® PS-3152 is a diethylene glycol-phthalic anhydride polyester polyol with a functionality of 2 and a hydroxyl number of 315 (Stepan Chemical Company).
Carpol® GP-5171: glycerin-initiated polyether polyol with a functionality of about 3, a hydroxyl number of 35, and an average molecular weight of about 5000; Carpol® GP-5015: glycerin-initiated polyether polyol with a functionality of 3, a hydroxyl number of 34, and an average molecular weight of about 5000; Carpol® GP-1500: glycerin-initiated polyether polyol with a functionality of 3, a hydroxyl number of 112, and an average molecular weight of about 1500; Carpol® GSP-280: sucrose polyether polyol based on glycerine, propylene oxide and ethylene oxide with a functionality of 7, a hydroxyl value of 280, and an average molecular weight of about 1400; Carpol® GSP-355: glycerine/sucrose initiated polyether polyol with a functionality of 4.5, a hydroxyl value of 355; Carpol® MX-470: mannich-based polyether polyol with a functionality of about 4, a hydroxyl number of 470, and an average molecular weight of 480; Carpol® GP-700: glycerine and propylene oxide polyether polyol with a functionality of 3, a hydroxyl number of 240, and an average molecular weight of about 700 (all Carpol® materials are products of Carpenter Company).
Terol® 250 is an aromatic polyester polyol with a functionality of 2 and a hydroxyl number in the range of 235 to 255 (Huntsman Corporation).
Dabco® DC193: silicone glycol surfactant; Dabco® T: amine with hydroxyl groups; Dabco® T-120: dibutylbis (dodecylthio) stannane; Dabco® PM-300: 2-butoxyethanol; Dabco® DC 5598: silicone glycol copolymer surfactant; Dabco® K-15: potassium octoate; Dabco® TMR: 2-hydroxypropyltrimethylammonium formate (all Dabco® materials are products of Air Products and Chemicals, Inc.).
Polycat® 204: amine catalyst (Air Products and Chemicals, Inc).
Tomamine® Q17-2 PG is an ether amine quaternary ammonia surfactant (75%) in isopropyl alcohol (Air Products and Chemicals, Inc.).
Tegostab® B 8871: polysiloxane copolymer; Tegostab® B 8407: polyether polydimethylsiloxane copolymer (both are products of Evonik Industries AG, Essen, Germany).
Jeffcat® ZR-70 is 2-(2-dimethylaminoethoxy)ethanol, an ethanol amine catalyst; Jeffcat® Z-110 is N,N,N'-trimethylaminoethyl-ethanolamine; Jeffcat® ZF-20 is bis-(2-dimethylaminoethyl)ether (all Jeffcat® materials are products of Huntsman Corp., The Woodlands, Tex.).

Pel-cat 9506 is a mixture of potassium octoate and potassium acetate; Pel-cat 9858-A is sodium hydroxy-nonylphenyl-N-methylglycinate (both are products of Elé Corporation).

Solstice® LBA: trans-1-chloro-3,3,3-trifluoropropene (Honeywell Inc.).

Genetron® 245fa: 1,1,1,3,3-pentafluoropropane (Honeywell Inc.).

Opteon™ 1100: 1,2-bis(trifluoromethyl)ethene; also called Formacel® 1100 (The Chemours Company).

Papi® 27: polymeric diphenylmethane diisocyanate (MDI) with 31.4 wt % NCO, viscosity 150 to 225 cps at 25° C., and an isocyanate equivalent weight of 134 (Dow Chemical Company).

Cone calorimetry measurements were performed on a Fire Testing Technology Dual Cone calorimeter according to ASTM E-1354. For all of the Examples, an incident heat flux of 40 kW/m$^2$ was used in the cone calorimetry tests for the Predicted Smoke Index calculations and an incident heat flux of 100 kW/m$^2$ was used in the cone calorimetry tests for the Predicted Flame Spread Index calculations. The Peak Heat Release Rate (PHRR), the maximum value of the heat released during combustion of the sample in the cone calorimeter, was measured. Values for the Peak Heat Release Rate are preferably less than 250. The ASTM E-84 burn profiles for predicted Smoke Index calculations and for predicted Flame Spread Index calculations were calculated from the cone calorimetry results. Using mathematical equations that were previously derived from a cone calorimeter and ASTM E-84 correlation study, the cone calorimeter results were converted into predicted numbers in the ASTM E-84. The target value for the Flame Spread Index was less than 25, preferably less than 20, and the target value for the Smoke Density Index was less than 450, preferably less than 200. The term "Smoke Index" is short for "smoke density developed", which is also referred to as "Smoke Developed Index" and "Smoke Density Index."

For some samples, the dimensional stability was determined; preferred volume changes in dimensional stability are ±15%. Some samples were subjected to a thermal conductivity test, and R values were calculated from the thermal conductivities. The R value (or R-value) is a measure of insulation efficiency or thermal resistance (the ability of a material to slow down heat transfer within itself), and is often used in the building and construction industry. The higher the R-value, the more a material prevents heat transfer. R-values for polyurethane foams are preferably about 6.5 or more.

Examples 1-22

The reported results in Examples 1-16 are an average of three lots with 5 samples per lot (a total of 15 samples for each test). The volume ratio of the A side to the B side in each run was 1:1, unless otherwise noted. The polyurethane foams of Examples 1-16 were prepared according to Procedure 1 below. The polyurethane foams of Examples 17-19 were prepared according to Procedure 2 below. The polyurethane foams of Examples 20-22 were prepared according to Procedure 1 below; the A side was Papi® 27 in all runs of Examples 1-22.

Procedure 1:

To form the B side, DBAA, polyols, surfactants, flame retardant, blowing agent and catalyst were weighed into a 0.5 gallon (1.9 L) reclosable container, and blended with a bow-tie agitator at 2000 rpm for 60 seconds or until a homogenous mixture with no visible phase separation was obtained. At a 450-g scale (total of A and B sides), the required amount of the B side mixture was weighed and added to a one-liter paper cup.

The polymeric MDI was wet-tared by weighing about 10% of its required amount into a 250-mL paper cup, pouring out the polymeric MDI within 3 seconds, re-taring the wet 250-mL cup and adding the full amount of the polymeric MDI. The polymeric MDI was then poured within a 3-second time span into the one-liter cup containing the B-side mixture, and the contents of the one liter paper cup were immediately mixed for 5 seconds at 2000 rpm. By this process, the amount of MDI used is within ±1% of the required amount.

While the foam was rising but before the foam reached the top of the one liter paper cup, the cup was inverted and held over a paper sheet. While the foam continued to rise, the cup was guided upwards without impeding the rising of the foam. Once the foam had sufficient strength to support itself and the cup, guiding of the cup was discontinued. After allowing the foam to sit for at least 24 hours, it was cut to generate specimens for cone calorimeter testing. Each specimen was weighed to determine the foam density.

Procedure 2:

To prepare each polyurethane foam, blends of the B-side components other than the catalyst(s) (DBAA, polyols, surfactants, flame retardant, and blowing agent) were made. The polyisocyanate and the B-side formulation were weighed into a 16 oz. (473 mL) paper cup and then mixed at 2000 rpm with a bow tie agitator for 15 seconds, at which point the catalyst(s) was injected into the mixture while the agitation continued. At the 20-second mark, the agitation was discontinued, and the reacting mixture was immediately poured into a 10-in×10-in×10-in (25.4 cm×25.4 cm×25.4 cm) wooden box mold that had been pre-lined with a polyethylene bag, and the box was closed. After 15 minutes, the cube-shaped foam encased in the polyethylene bag was removed from the mold. After allowing the foam to sit for at least 24 hours, it was cut to generate the specimens for cone calorimeter testing. Each specimen was weighed to determine the foam density. The catalyst was added after the A side and B side were brought into contact, which is related to handling and timing on the laboratory scale; at larger scales, the catalyst is included in the B side formulations.

In Examples 1-4, open-cell spray polyurethane foams were prepared. Examples 2 and 3 are comparative. Amounts of the components and process information are listed in Table 1; test results are summarized in Table 2. In Examples 1-4, water was the only blowing agent.

In Examples 5-10, closed-cell spray polyurethane foams were prepared. Examples 5, 6, 8, and 9 are comparative. In Example 9, the Saytex® RB-79 flame retardant was added as a solution in 2-butoxyethanol. Amounts of the components and process information are listed in Table 3; test results are summarized in Table 4.

In Examples 11-16, closed-cell spray polyurethane foams were prepared. Examples 12-16 are comparative. Amounts of the components and process information are listed in Table 5; test results are summarized in Table 6.

In Examples 17-19, panel polyurethane foams were prepared. Examples 17 and 18 are comparative. Amounts of the components and process information are listed in Table 7; test results are summarized in Table 8.

In Examples 20-22, closed-cell spray polyurethane foams were prepared. Run 1 of Example 21 and runs 1 and 2 of Example 22 are comparative. Amounts of the components and process information for Examples 20-22 are listed in Tables 9A-B, 11A-B, and 13A-C; test results for Examples 20-22 are summarized in Tables 10A-B, 12A-B, and 14A-C.

TABLE 1

| Example | 1 | 2 | 3 | 4 |
|---|---|---|---|---|
| B side | | | | |
| DBAA | 5.45 | — | — | 5.50 |
| Saytex ® RB-79 | — | 8.67 | — | — |
| TCPP | — | — | 30.00 | — |
| 2-butoxyethanol | 4.95 | 4.78 | — | 4.00 |
| Sucrose in water (67%) | 69.35 | 67.00 | 50.50 | 69.46 |
| Carpol ® GP-5171 | 4.95 | 4.78 | 5.00 | 5.00 |
| Jeffcat ® ZR-70 | 5.75 | 5.55 | 5.80 | 6.40 |
| Tegostab ® B 8407 | 1.85 | 1.77 | 1.85 | 1.85 |
| Tegostab ® B 8871 | 1.85 | 1.77 | 1.85 | 1.85 |
| Tomamine ® Q17-2 PG | 0.93 | 0.90 | — | 0.94 |
| Water | 4.95 | 4.78 | 5.00 | 5.00 |
| A-Side | | | | |
| Papi ® 27 | 100.00 | 100.00 | 100.00 | 100.00 |
| Process | | | | |
| A:B Weight Ratio | 104.2:100 | 103.7:100 | 103.5:100 | 104.1:100 |
| Isocyanate Index | 27.3 | 28.0 | 35.1 | 27.2 |

TABLE 2

| Example | 1 | 2 | 3 | 4 |
|---|---|---|---|---|
| Foam properties | | | | |
| Density, lb/ft$^3$ | 0.81 | 0.70 | 0.60 | 0.62 |
| Density, kg/m$^3$ | 13.0 | 11.2 | 9.6 | 9.9 |
| Dimensional Stability* (% vol. change) | 0.5 | −0.5 | −5.1 | 0.5 |
| Predicted Flame Spread Index | 24 | 24 | 23 | 24 |
| Predicted Smoke Density Index | 18 | 11 | 45 | 17 |
| Predicted Fire Rating | Class 1 | Class 1 | Class 1 | Class 1 |

*Dimensional stability was measured at 70° C. for 14 days at 95% RH.

Tables 1 and 2 show that much lower amounts of DBAA can be used relative to TCPP and RB-79 in open cell foams to achieve a Class 1 flame retardant rating for the foam. The polyurethane foams containing DBAA had a much better dimensional stability than the foams containing TCPP or Saytex® RB-79 flame retardant.

TABLE 3

| | Example | | | | | |
|---|---|---|---|---|---|---|
| | 5 | 6 | 7 | 8 | 9 | 10 |
| B-side | | | | | | |
| DBAA | — | — | 8.11 | — | — | 8.11 |
| Saytex ® RB-79 | 6.76 | 13.33 | — | 6.76 | — | — |
| TCPP | 8.26 | — | — | 8.26 | — | — |
| 2-butoxyethanol | — | — | — | — | — | — |
| Terate ® HT 5503 | 40.00 | 39.26 | 41.94 | 38.00 | 25.75 | 41.94 |
| Voranol ® 490 | 28.47 | 30.01 | 32.06 | 30.52 | 12.00 | 32.08 |
| Carpol ® GSP-355 | — | — | — | — | 22.00 | — |
| Dabco ® DC193 | 2.00 | 2.00 | 2.00 | 2.00 | 2.00 | 2.00 |
| Dabco ® T | 3.00 | 3.00 | 3.00 | 3.00 | 3.00 | 3.00 |
| Dabco ® PM-300 | 2.00 | 2.00 | 2.00 | 2.00 | 2.00 | 2.00 |
| Water | 2.07 | 1.90 | 1.80 | 2.02 | 1.85 | 1.76 |
| Genetron ® 245fa | 7.44 | 8.5 | 9.10 | — | — | — |
| Solstice ® LBA | — | — | — | 7.44 | 8.45 | 9.10 |
| A-side | | | | | | |
| Papi ® 27 | 100.00 | 100.00 | 100.00 | 100.00 | 100.00 | 100.00 |
| Process | | | | | | |
| A:B Weight Ratio | 1.044:1 | 1.027:1 | 1.035:1 | | | |
| Isocyanate Index | 110.1 | 105.9 | 106.2 | 109.9 | 110.1 | 106.6 |

TABLE 4

| | Example | | | | | |
|---|---|---|---|---|---|---|
| | 5 | 6 | 7 | 8 | 9 | 10 |
| Foam properties | | | | | | |
| Density (lb/ft$^3$) | 1.57 | 1.64 | 1.80 | 1.68 | 1.75 | 1.99 |
| Density (kg/m$^3$) | 25.1 | 26.3 | 28.8 | 26.6 | 28.0 | 31.9 |
| Compressive Strength (kPa) | 94.5 | 86.2 | 101.4 | 94.5 | 85.5 | 124.1 |
| R-value (/inch) | 6.34 | 6.35 | 6.74 | 6.8 | 6.7 | 7.1 |
| R-value (m$^2$K/W) | 1.117 | 1.118 | 1.187 | 1.98 | 1.80 | 1.250 |
| Predicted Flame Spread Index | 21.4 | 23 | 24 | 27 | 27 | 31 |
| Predicted Smoke Density Index | 101 | 185 | 49 | 304 | 105 | 56 |
| Predicted Fire Rating | Class 1 | Class 1 | Class 1 | | | |

Tables 3 and 4 show that much lower amounts of DBAA can be used relative to RB-79 alone or combinations of TCPP and RB-79 in closed cell foams to achieve a Class 1 flame retardant rating for the foam. The polyurethane foams containing DBAA had improved R-values as compared to the foams containing TCPP and/or Saytex® RB-79 flame retardant.

TABLE 5

| | Example | | | | | |
|---|---|---|---|---|---|---|
| | 11 | 12 | 13 | 14 | 15 | 16 |
| B-side | | | | | | |
| DBAA | 8.11 | — | — | — | — | — |
| 2,3-dibromo-2-butene-1,4-diol | — | 9.23 | 4.44 | 9.23 | — | — |
| Saytex ® RB-79 | — | — | — | — | 12.00 | 6.75 |
| TCPP | — | — | 8.57 | — | — | 8.25 |
| Terol ® 250 | 46.60 | 45.93 | 32.21 | 42.21 | 43.58 | 43.58 |
| Carpol ® GSP-280 | — | — | — | 9.79 | — | — |
| Carpol ® MX-470 | 14.38 | — | — | — | — | — |
| Carpol ® GP-700 | — | 15.27 | — | 19.05 | 5.00 | — |
| Voranol ® 370 | 17.42 | — | 36.83 | — | — | — |
| Voranol ® 490 | — | 16.07 | — | — | 24.77 | 28.07 |
| Diethylene glycol | — | — | — | — | — | 1.7 |
| Dabco ® PM-300 | 2.00 | 2.00 | 2.30 | 2.00 | 3.00 | — |
| Dabco ® DC193 | 2.00 | 2.00 | 2.00 | 2.00 | 2.00 | 2.00 |
| Diglycolamine | — | — | 2.96 | 6.15 | — | — |
| Dabco ® T | 2.00 | 2.00 | 3.00 | 2.00 | 2.00 | 2.00 |
| Water | 1.66 | 1.67 | 1.69 | 1.67 | 1.65 | 1.65 |
| Solstice ® LBA | 5.83 | 5.83 | 6.00 | 5.90 | 6.00 | 6.00 |
| A-side | | | | | | |
| Papi ® 27 | 100.00 | 100.00 | 100.00 | 100.00 | 100.00 | 100.00 |
| Process | | | | | | |
| A:B Weight Ratio | 102:100 | 103:100 | 104.5:100 | 104.1:100 | 102.6:100 | 102.5:100 |
| Isocyanate Index | 109.9 | 109.9 | 111.6 | 107 | 110 | 110 |

TABLE 6

| Example | 11 | 12 | 13 | 14 | 15 | 16 |
|---|---|---|---|---|---|---|
| Foam Properties | | | | | | |
| Density (lb/ft³) | 2.06 | 1.98 | 2.01 | 2.33 | 1.82 | 1.82 |
| Density (kg/m³) | 33.0 | 31.7 | 32.2 | 37.3 | 29.2 | 29.2 |
| Compressive Strength (kPa) | 117.2 | 109.6 | — | 84.8 | 66.9 | 91.0 |
| R-value (/inch) | 6.45 | — | — | 6.50 | 6.62 | 6.84 |
| R-value (m²K/W) | 1.136 | — | — | 1.145 | 1.662 | 1.205 |
| Predicted Flame Spread Index | 21.9 | 22.4 | 17.5 | 19.2 | 22.2 | 20.4 |
| Predicted Smoke Density Index | 33 | 31 | 123 | 47 | 15 | 55 |
| Predicted Fire Rating | Class 1 | Class 1 | Class 1 | Class 1 | Class 1 | Class 1 |

TABLE 7

| Example | 17 | 18 | 19 |
|---|---|---|---|
| B-side | | | |
| DBAA | — | — | 15.02 |
| Saytex ® RB-79 | — | 8.56 | — |
| TCPP | 14.96 | — | — |
| DE | — | 0.95 | — |
| Stepanpol ® PS-3152 | 62.67 | 36.72 | — |
| Carpol ® GSP-280 | — | — | 66.21 |
| Voranol ® 370 | — | 34.42 | — |
| Dabco ® DC 5598 | 1.25 | 1.27 | 1.23 |
| Dabco ® K-15 | 1.14 | 1.86 | 1.81 |
| Pel-cat 9506 | 1.96 | — | — |
| Pel-cat 9858-A | 0.89 | — | — |
| Jeffcat ® Z-110 | 0.21 | — | — |
| Jeffcat ® ZF-20 | 0.37 | — | — |
| Dabco ® TMR-2 | — | 1.24 | 1.21 |
| Dabco ® T | — | 0.65 | 0.62 |
| Water | 0.17 | 0.94 | 0.91 |
| N-Pentane/isopentane (50/50) | 16.38 | 13.40 | 13.00 |
| A-side | | | |
| Papi ® 27 | 100.00 | 100.00 | 100.00 |
| Process | | | |
| A:B Volume Ratio | 131.1:100 | 145.8:100 | 142.4:100 |
| A:B Weight Ratio | 153.4:100 | 169.1:100 | 164:100 |
| Isocyanate Index | 297.8 | 208.9 | 232.7 |

TABLE 8

| Example | 17 | 18 | 19 |
|---|---|---|---|
| Foam Properties | | | |
| Density (lb/ft³) | 1.90 | 2.0 | 1.95 |
| Density (kg/m³) | 30.4 | 32.0 | 31.2 |
| Compressive Strength (kPa) | 187 | 314 | 214 |
| R-value (/inch) | 6.2 | 6.8 | 5.25 |

TABLE 8-continued

| Example | 17 | 18 | 19 |
|---|---|---|---|
| R-value (m²K/W) | 1.092 | 1.198 | 0.925 |
| Predicted Flame Spread Index | 21 | 22 | 22.5 |
| Predicted Smoke Density Index | 25 | 48 | 439 |
| Predicted Fire Rating | Class 1 | Class 1 | Class 1 |

Tables 7 and 8 show that using DBAA in panel foams achieves a Class 1 flame retardant rating for the foam.

TABLE 9A

| Example 20-Run | 1 | 2 | 3 | 4 | 5 | 6 | 7 | 8 | 9 | 10 |
|---|---|---|---|---|---|---|---|---|---|---|
| B side | | | | | | | | | | |
| Viscosity (cPs; at 25° C.) | 255 | 410 | 250 | 170 | 200 | 245 | 1325 | 1440 | 1050 | 180 |
| DBAA | 0.69 | 0.69 | 5.45 | 7.32 | 7.32 | 7.32 | 7.63 | 7.63 | 7.95 | 9.41 |
| Terate ® HT 5349 | 51.61 | 51.61 | 51.61 | 47.36 | 47.36 | 47.36 | 51.61 | 51.61 | 48.04 | 42.88 |
| Voranol ® 370 | 0.14 | 0.14 | 1.09 | 1.46 | 1.46 | 1.46 | 0.80 | 0.80 | 1.58 | 1.88 |
| Carpol ® GSP-280 | 26.21 | 26.21 | 21.45 | 23.83 | 23.83 | 23.83 | 25.53 | 25.53 | 26.21 | 26.21 |
| Dabco ® DC193 | 2.00 | 2.00 | 2.00 | 2.00 | 2.00 | 2.00 | 2.00 | 2.00 | 2.00 | 2.00 |
| Dabco ® K-15 | 0.25 | 0.25 | 0.25 | 0.25 | 0.25 | 0.25 | 0.25 | 0.25 | 0.25 | 0.25 |
| Dabco ® T-120 | 0.25 | 0.25 | 0.25 | 0.25 | 0.25 | 0.25 | 0.25 | 0.25 | 0.25 | 0.25 |
| Polycat ® 204 | 4.00 | 4.00 | 4.00 | 4.00 | 4.00 | 4.00 | 4.00 | 4.00 | 4.00 | 4.00 |
| Water | 0.08 | 0.08 | 0.08 | 0.08 | 0.08 | 0.08 | 0.86 | 0.86 | 0.60 | 0.08 |
| Genetron ® 245fa | 15.00 | 15.00 | 15.00 | 15.00 | 15.00 | 15.00 | 8.74 | 8.74 | 11.31 | 15.00 |
| Process | | | | | | | | | | |
| A:B vol. ratio | 1:1 | 1:1 | 1:1 | 1:1 | 1:1 | 1:1 | 1:1 | 1:1 | 1:1 | 1:1 |
| Isocyanate Index | 1.335 | 1.335 | 1.313 | 1.314 | 1.315 | 1.315 | 1.086 | 1.086 | 1.171 | 1.314 |

TABLE 9B

| Example 20-Run | 11 | 12 | 13 | 14 | 15 | 16 | 17 | 18 | 19 | 20 |
|---|---|---|---|---|---|---|---|---|---|---|
| B side | | | | | | | | | | |
| Viscosity (cPs; at 25° C.) | 865 | 925 | 190 | 1290 | 930 | 65 | 920 | 965 | 1450 | 1540 |
| DBAA | 7.79 | 8.87 | 9.18 | 9.39 | 11.09 | 11.82 | 12.00 | 12.00 | 12.00 | 12.00 |
| Terate ® HT 5349 | 51.26 | 44.79 | 46.02 | 48.71 | 47.96 | 42.30 | 43.69 | 43.69 | 48.30 | 51.61 |
| Voranol ® 370 | 1.95 | 2.22 | 2.29 | 2.35 | 2.77 | 2.95 | 3.00 | 3.00 | 3.00 | 3.00 |
| Carpol ® GSP-280 | 21.45 | 26.21 | 21.45 | 25.36 | 21.45 | 21.45 | 24.28 | 24.28 | 26.21 | 22.90 |
| Dabco ® DC193 | 2.00 | 2.00 | 2.00 | 2.00 | 2.00 | 2.00 | 2.00 | 2.00 | 2.00 | 2.00 |
| Dabco ® K-15 | 0.25 | 0.25 | 0.25 | 0.25 | 0.25 | 0.25 | 0.25 | 0.25 | 0.25 | 0.25 |
| Dabco ® T-120 | 0.25 | 0.25 | 0.25 | 0.25 | 0.25 | 0.25 | 0.25 | 0.25 | 0.25 | 0.25 |
| Polycat ® 204 | 4.00 | 4.00 | 4.00 | 4.00 | 4.00 | 4.00 | 4.00 | 4.00 | 4.00 | 4.00 |
| Water | 0.62 | 0.57 | 0.00 | 1.08 | 0.72 | 0.08 | 0.67 | 0.67 | 1.59 | 1.59 |
| Genetron ® 245fa | 11.06 | 11.41 | 14.57 | 7.71 | 10.24 | 15.00 | 10.54 | 10.54 | 4.00 | 4.00 |
| Process | | | | | | | | | | |
| A:B vol. ratio | 1:1 | 1:1 | 1:1 | 1:1 | 1:1 | 1:1 | 1:1 | 1:1 | 1:1 | 1:1 |
| Isocyanate Index | 1.148 | 1.167 | 1.307 | 1.048 | 1.111 | 1.292 | 1.124 | 1.124 | 0.947 | 0.941 |

TABLE 10A

| Example 20-Run | 1 | 2 | 3 | 4 | 5 | 6 | 7 | 8 | 9 | 10 |
|---|---|---|---|---|---|---|---|---|---|---|
| Density, lb/ft³ | 2.12 | 2.22 | 2.12 | 2.13 | 2.28 | 2.05 | 1.96 | 1.95 | 2.04 | 2.1 |
| Density, kg/m³ | 34.0 | 35.6 | 34.0 | 34.1 | 36.5 | 32.8 | 31.4 | 31.2 | 32.7 | 33.6 |
| Dimensional stability[1] (vol. change) | 7.29 | 5.55 | 3.75 | 5.58 | 7.49 | 4.44 | 2.27 | −3.04 | −4.00 | 5.69 |
| Compressive Strength, psi | 21.2 | 25.8 | 22.2 | 20.3 | 22.5 | 20.9 | 26.1 | 18.9 | 19.7 | 19.6 |
| Compressive Strength, kPa | 146.2 | 177.9 | 153.1 | 140.0 | 155.1 | 144.1 | 180.0 | 130.3 | 135.8 | 135.1 |
| R-value, /in. | 7.42 | 7.23 | 7.64 | 7.27 | 7.84 | 7.44 | 4.54 | 6.82 | 7.07 | 7.19 |

TABLE 10A-continued

| Example 20-Run | 1 | 2 | 3 | 4 | 5 | 6 | 7 | 8 | 9 | 10 |
|---|---|---|---|---|---|---|---|---|---|---|
| R-value, m²K/W | 1.307 | 1.273 | 1.345 | 1.280 | 1.381 | 1.310 | 0.800 | 1.201 | 1.245 | 1.266 |
| Peak Heat Release Rate | 288 | 276 | 238 | 234 | 224 | 235 | 235 | 245 | 242 | 226 |
| Predicted Flame Spread Index | 25.4 | 23.0 | 22.3 | 21.2 | 21.9 | 20.8 | 21.3 | 23.0 | 23.9 | 21.3 |
| Predicted Smoke Index | 153 | 89 | 47 | 19 | 28 | 52 | 28 | 24 | 30 | 35 |

[1] Dimensional stability was measured at 70° C. for 14 days at 95% RH.

TABLE 10B

| Example 20-Run | 11 | 12 | 13 | 14 | 15 | 16 | 17 | 18 | 19 | 20 |
|---|---|---|---|---|---|---|---|---|---|---|
| Density, lb/ft³ | 2.02 | 1.96 | 2.1 | 1.87 | 1.89 | 1.94 | 1.93 | 1.95 | 1.92 | 1.89 |
| Density, kg/m³ | 32.4 | 31.4 | 33.6 | 30.0 | 30.3 | 31.1 | 30.9 | 31.2 | 30.8 | 30.3 |
| Dimensional stability[1] (vol. change) | 1.00 | −1.10 | 6.37 | −0.12 | −2.47 | 7.20 | −0.26 | −2.74 | 0.41 | 2.33 |
| Compressive Strength, psi | 20.1 | 17.0 | 17.9 | 24.4 | 17.9 | 16.4 | 16.6 | 17.9 | 21.2 | 22.0 |
| Compressive Strength, kPa | 138.6 | 117.2 | 123.4 | 168.2 | 123.4 | 113.1 | 114.5 | 123.4 | 146.2 | 151.7 |
| R-value, /in. | 7.4 | 7.03 | 7.43 | 4.8 | 7.06 | 7.39 | 7.09 | 6.98 | 4.86 | 4.75 |
| R-value, m²K/W | 1.303 | 1.238 | 1.308 | 0.845 | 1.243 | 1.301 | 1.249 | 1.229 | 0.856 | 0.837 |
| Peak Heat Release Rate | 247 | 231 | 211 | 226 | 226 | 229 | 203 | 200 | 222 | 231 |
| Predicted Flame Spread Index | 22.2 | 21.1 | 20.7 | 22.1 | 22.9 | 22.7 | 20.2 | 21.5 | 19.1 | 21.2 |
| Predicted Smoke Index | 48 | 18 | 22 | 27 | 18 | 29 | 17 | 21 | 28 | 37 |

[1] Dimensional stability was measured at 70° C. for 14 days at 95% RH.

TABLE 11A

| Example 21-Run | 1[1] | 2 | 3 | 4 | 5 | 6 | 7 |
|---|---|---|---|---|---|---|---|
| B side | | | | | | | |
| Viscosity (cPs; at 25° C.) | 1715 | 1350 | 1265 | 1275 | 1115 | 1125 | 965 |
| DBAA | 0 | 4.52 | 4.55 | 6.92 | 7.03 | 7.03 | 8.38 |
| Terate ® HT 5349 | 40.69 | 51.22 | 51.61 | 50.32 | 51.61 | 51.61 | 47.31 |
| Voranol ® 280 | — | 26.01 | 26.21 | 26.21 | 23.11 | 23.11 | 25.72 |
| Voranol ® 370 | 23.91 | 1.13 | 1.14 | 1.73 | 1.76 | 1.76 | 2.10 |
| Dabco ® DC193 | 2.00 | 2.00 | 2.00 | 2.00 | 2.00 | 2.00 | 2.00 |
| Dabco ® T-120 | 0.25 | 0.25 | 0.25 | 0.25 | 0.25 | 0.25 | 0.25 |
| Dabco ® K-15 | 0.25 | 0.25 | 0.25 | 0.25 | 0.25 | 0.25 | 0.25 |
| Polycat ® 204 | 4.00 | 4.00 | 4.00 | 4.00 | 4.00 | 4.00 | 4.00 |
| Water | 1.00 | 0.76 | 0.80 | 1.05 | 0.80 | 0.80 | 0.80 |
| Solstice ® LBA Process | 10.00 | 10.00 | 10.00 | 8.32 | 10.00 | 10.00 | 10.00 |
| A:B vol. ratio | 1:1 | 1:1 | 1:1 | 1:1 | 1:1 | 1:1 | 1:1 |
| Isocyanate Index | 1.078 | 1.139 | 1.164 | 1.098 | 1.144 | 1.144 | 1.147 |

| Example 21-Run | 8 | 9 | 10 | 11 | 12[2] | 13 |
|---|---|---|---|---|---|---|
| B side | | | | | | |
| Viscosity (cPs; at 25° C.) | 1010 | 1610 | 1590 | 1165 | 1265 | 1395 |
| DBAA | 8.38 | 8.54 | 8.54 | 9.57 | 9.57 | 9.43 |
| Terate ® HT 5349 | 47.31 | 51.61 | 51.61 | 46.92 | 46.92 | 48.69 |
| Voranol ® 280 | 25.72 | 25.75 | 25.75 | — | — | 26.21 |
| Voranol ® 370 | 2.10 | 2.13 | 2.13 | 26.22 | 26.22 | 2.43 |
| Dabco ® DC193 | 2.00 | 2.00 | 2.00 | 2.00 | 2.00 | 2.00 |
| Dabco ® T-120 | 0.25 | 0.25 | 0.25 | 0.25 | 0.25 | 0.25 |
| Dabco ® K-15 | 0.25 | 0.25 | 0.25 | 0.25 | 0.25 | 0.25 |
| Polycat ® 204 | 4.00 | 4.00 | 4.00 | 4.00 | 4.00 | 4.00 |

TABLE 11A-continued

|  | | | | | | |
|---|---|---|---|---|---|---|
| Water | 0.80 | 1.43 | 1.43 | 0.80 | 0.80 | 1.29 |
| Solstice ® LBA Process | 10.00 | 5.48 | 5.48 | 10.00 | 10.00 | 6.45 |
| A:B vol. ratio | 1:1 | 1:1 | 1:1 | 1:1 | 1:1 | 1:1 |
| Isocyanate Index | 1.147 | 1.015 | 1.015 | 1.049 | 1.052 | 1.04 |

[1] Comparative run.
[2] Contains 9% of a mixed ester of tetrabromophthalic anhydride with diethylene glycol and propylene glycol (Saytex ® RB-79 flame retardant) and 6% tris(1-chloro-2-propyl)phosphate (TCPP).

TABLE 11B

| Example 21-Run | 14 | 15 | 16 | 17 | 18 | 19 | 20 |
|---|---|---|---|---|---|---|---|
| B side | | | | | | | |
| Viscosity (cPs; at 25° C.) | 1080 | 1655 | 1660 | 1085 | 1145 | 900 | 2070 |
| DBAA | 10.51 | 10.72 | 10.77 | 11.07 | 11.07 | 11.24 | 12.00 |
| Terate ® HT 5349 | 47.61 | 50.33 | 48.28 | 49.75 | 49.75 | 45.02 | 51.61 |
| Voranol ® 280 | 24.11 | 26.21 | 25.23 | 21.45 | 21.45 | 26.21 | 26.21 |
| Voranol ® 370 | 2.63 | 2.68 | 2.69 | 2.77 | 2.77 | 2.81 | 3.00 |
| Carpol ® GSP-280 | — | — | — | — | — | — | — |
| Carpol ® GP-5015 | — | — | — | — | — | — | — |
| Dabco ® DC193 | 2.00 | 2.00 | 2.00 | 2.00 | 2.00 | 2.00 | 2.00 |
| Dabco ® T-120 | 0.25 | 0.25 | 0.25 | 0.25 | 0.25 | 0.25 | 0.25 |
| Dabco ® K-15 | 0.25 | 0.25 | 0.25 | 0.25 | 0.25 | 0.25 | 0.25 |
| Polycat ® 204 | 4.00 | 4.00 | 4.00 | 4.00 | 4.00 | 4.00 | 4.00 |
| Water | 0.96 | 1.70 | 1.40 | 0.98 | 0.97 | 1.02 | 2.10 |
| Solstice ® LBA Process | 8.65 | 3.56 | 5.24 | 8.48 | 8.48 | 8.23 | 0.69 |
| A:B vol. ratio | 1:1 | 1:1 | 1:1 | 1:1 | 1:1 | 1:1 | 1:1 |
| Isocyanate Index | 1.096 | 0.962 | 0.983 | 1.081 | 1.083 | 1.086 | 0.897 |

| Example 21-Run | 21 | 22 | 23 | 24 | 25 | 26 |
|---|---|---|---|---|---|---|
| B side | | | | | | |
| Viscosity (cPs; at 25° C.) | 1605 | 1590 | 1355 | 1075 | 820 | 1395 |
| DBAA | 12.00 | 12.00 | 12.00 | 12.00 | 12.00 | 10.92 |
| Terate ® HT 5349 | 51.61 | 51.61 | 47.17 | 45.22 | 42.30 | 48.96 |
| Voranol ® 280 | 23.25 | 23.25 | 25.69 | 23.29 | 26.21 | — |
| Voranol ® 370 | 3.00 | 3.00 | 3.00 | 3.00 | 3.00 | — |
| Carpol ® GSP-280 | — | — | — | — | — | 16.95 |
| Carpol ® GP-5015 | — | — | — | — | — | 10.00 |
| Dabco ® DC193 | 2.00 | 2.00 | 2.00 | 2.00 | 2.00 | 2.00 |
| Dabco ® T-120 | 0.25 | 0.25 | 0.25 | 0.25 | 0.25 | 0.25 |
| Dabco ® K-15 | 0.25 | 0.25 | 0.25 | 0.25 | 0.25 | 0.25 |
| Polycat ® 204 | 4.00 | 4.00 | 4.00 | 4.00 | 4.00 | 4.00 |
| Water | 1.65 | 1.65 | 1.38 | 0.76 | 0.77 | 1.36 |
| Solstice ® LBA Process | 3.65 | 3.65 | 5.64 | 10.00 | 10.00 | 5.31 |
| A:B vol. ratio | 1:1 | 1:1 | 1:1 | 1:1 | 1:1 | 1:1 |
| Isocyanate Index | 0.957 | 0.956 | 1.01 | 1.132 | 1.14 | 1.059 |

TABLE 12A

| Example 21-Run | 1[1] | 2 | 3 | 4 | 5 | 6 | 7 |
|---|---|---|---|---|---|---|---|
| Density, lb/ft$^3$ | 1.95 | 2.07 | 2.02 | 1.98 | 1.94 | 2.01 | 2.05 |
| Density, kg/m$^3$ | 31.2 | 33.2 | 32.4 | 31.7 | 31.1 | 32.2 | 32.8 |
| Dimensional stability[2] (vol. change) | −11.8 | 0.64 | 1.07 | −3.67 | −1.09 | −1.11 | −0.74 |
| Compressive Strength, psi | 26.0 | 20.1 | 18.63 | 18.13 | 17.50 | 18.27 | 19.40 |
| Compressive Strength, kPa | 179.3 | 138.6 | 128.4 | 125.0 | 120.7 | 126.0 | 133.8 |
| R-value, /in. | 7.29 | 7.07 | 7.27 | 7.35 | 7.3 | 7.37 | 7.17 |

TABLE 12A-continued

| | | | | | | | |
|---|---|---|---|---|---|---|---|
| R-value, m²K/W | 1.284 | 1.245 | 1.280 | 1.294 | 1.286 | 1.298 | 1.263 |
| Peak Heat Release Rate | 184 | 240 | 226 | 212 | 198 | 248 | 198 |
| Predicted Flame Spread Index | 19.8 | 21.4 | 22.1 | 21.9 | 21.1 | 23.3 | 20.9 |
| Predicted Smoke Index | 15 | 22 | 19 | 27 | 18 | 22 | 29 |

| Example 21-Run | 8 | 9 | 10 | 11 | 12 | 13 |
|---|---|---|---|---|---|---|
| Density, lb/ft³ | 1.95 | 1.94 | 2.04 | 1.81 | 1.91 | 1.99 |
| Density, kg/m³ | 31.2 | 31.1 | 32.7 | 29.0 | 30.6 | 31.9 |
| Dimensional stability² (vol. change) | −2.93 | −19.04 | −16.27 | −0.15 | — | −14.24 |
| Compressive Strength, psi | 19.63 | 17.93 | 19.63 | 24.7 | — | 18.10 |
| Compressive Strength, kPa | 135.3 | 123.6 | 135.3 | 170.3 | — | 124.8 |
| R-value, /in. | 7.67 | 6.89 | 7.03 | 4.78 | 7.92 | 6.99 |
| R-value, m²K/W | 1.351 | 1.213 | 1.238 | 0.842 | 1.395 | 1.231 |
| Peak Heat Release Rate | 215 | 233 | 221 | 228 | 214 | 219 |
| Predicted Flame Spread Index | 19.6 | 24.0 | 21.0 | 19.9 | 18.6 | 22.9 |
| Predicted Smoke Index | 36 | 21 | 25 | 88 | 13 | 16 |

[1]Comparative run.
[2]Dimensional stability was measured at 70° C. for 14 days at 95% RH.

TABLE 12B

| Example 21-Run | 14 | 15 | 16 | 17 | 18 | 19 | 20 |
|---|---|---|---|---|---|---|---|
| Density, lb/ft³ | 1.98 | 1.86 | 1.89 | 1.75 | 1.94 | 1.93 | 1.92 |
| Density, kg/m³ | 31.7 | 29.8 | 30.3 | 28.0 | 31.1 | 30.9 | 30.8 |
| Dimensional stability¹ (vol. change) | −4.52 | −43.42 | 1.62 | 3.36 | 0.33 | −4.74 | −69.19 |
| Compressive Strength, psi | 16.37 | 17.37 | 22.2 | 23.37 | 17.03 | 19.23 | 16.67 |
| Compressive Strength, kPa | 112.9 | 119.8 | 153.1 | 161.1 | 117.4 | 132.6 | 114.9 |
| R-value, /in. | 7.53 | 6.72 | 4.52 | 5.05 | 7.15 | 4.98 | 6.22 |
| R-value, m²K/W | 1.326 | 1.183 | 0.796 | 0.889 | 1.259 | 0.877 | 1.095 |
| Peak Heat Release Rate | 214 | 210 | 238 | 197 | 210 | 192 | 197 |
| Predicted Flame Spread Index | 19.8 | 21.4 | 20.1 | 19.0 | 19.1 | 19.0 | 21.5 |
| Predicted Smoke Index | 17 | 48 | 109 | 38 | 42 | 43 | 58 |

| Example 21-Run | 21 | 22 | 23 | 24 | 25 | 26 |
|---|---|---|---|---|---|---|
| Density, lb/ft³ | 1.89 | 2.02 | 1.99 | 1.86 | 1.96 | 1.90 |
| Density, kg/m³ | 30.3 | 32.4 | 31.9 | 29.8 | 31.4 | 30.4 |
| Dimensional stability¹ (vol. change) | −14.89 | −24.33 | 2.12 | 0.07 | −0.22 | −39.22 |
| Compressive Strength, psi | 19.00 | 15.23 | 26.50 | 22.90 | 17.43 | 9.5 |
| Compressive Strength, kPa | 131.0 | 105.0 | 182.7 | 157.9 | 99.5 | 65.5 |
| R-value, /in. | 5.55 | 6.35 | 4.99 | 7.18 | 7.25 | 6.50 |
| R-value, m²K/W | 0.977 | 1.118 | 0.879 | 1.264 | 1.277 | 1.145 |
| Peak Heat Release Rate | 197 | 204 | 201 | 193 | 187 | 453 |
| Predicted Flame Spread Index | 19.3 | 20.1 | 17.5 | 18.1 | 18.7 | 21.6 |
| Predicted Smoke Index | 32 | 50 | 56 | 76 | 49 | 1074 |

[1]Dimensional stability was measured at 70° C. for 14 days at 95% RH.

TABLE 13A

| Example 22-Run | 1* | 2* | 3 | 4 | 5 | 6 | 7 | 8 |
|---|---|---|---|---|---|---|---|---|
| B side | | | | | | | | |
| Viscosity (cPs; at 25° C.) | 4010 | 1560 | 1775 | 1635 | 2435 | 1645 | 2895 | 2750 |
| DBAA | 0.00 | 0.00 | 1.23 | 2.80 | 5.37 | 6.60 | 8.00 | 8.00 |
| Terate ® HT 5349 | 64.74 | 52.75 | 64.74 | 64.35 | 62.72 | 48.93 | 60.00 | 60.00 |
| Voranol ® 280 | — | — | — | — | — | — | — | — |
| Voranol ® 370 | — | — | 0.31 | 0.70 | 1.34 | 1.65 | 2.00 | 2.00 |
| Carpol ® GSP-280 | 29.95 | 29.95 | 16.43 | 16.43 | 22.84 | 29.95 | — | 7.14 |
| Carpol ® GP-5015 | — | — | — | — | — | — | 16.05 | 8.92 |
| Carpol ® GP-700 | — | — | — | — | — | — | — | — |
| Vorasurf ® 504 | — | — | — | — | — | — | — | — |
| Dabco ® DC193 | 2.00 | 2.00 | 2.00 | 2.00 | 2.00 | 2.00 | 2.00 | 2.00 |
| Dabco ® T-120 | 0.25 | 0.25 | 0.25 | 0.25 | 0.25 | 0.25 | 0.25 | 0.25 |
| Dabco ® K-15 | 0.25 | 0.25 | 0.25 | 0.25 | 0.25 | 0.25 | 0.25 | 0.25 |
| Polycat ® 204 | 4.00 | 4.00 | 4.00 | 4.00 | 4.00 | 4.00 | 4.00 | 4.00 |
| Water | 2.26 | 0.89 | 0.86 | 1.04 | 1.94 | 1.36 | 1.45 | 1.44 |
| Opteon ™ 1100 | 0.01 | 12.00 | 12.00 | 10.43 | 2.43 | 7.56 | 6.00 | 6.00 |
| Process | | | | | | | | |
| A:B vol. ratio | 1:1 | 1:1 | 1:1 | 1:1 | 1:1 | 1:1 | 1:1 | 1:1 |
| Isocyanate Index | 0.899 | 1.156 | 1.128 | 1.082 | 0.917 | 1.026 | 1.083 | 1.031 |

| Example 22-Run | 9 | 10 | 11 | 12 | 13 | 14 | 15 | 16 |
|---|---|---|---|---|---|---|---|---|
| B side | | | | | | | | |
| Viscosity (cPs; at 25° C.) | 2455 | 1620 | 1575 | 1585 | 1625 | 1425 | 955 | 1625 |
| DBAA | 8.00 | 8.61 | 8.61 | 8.61 | 8.61 | 9.83 | 9.85 | 9.85 |
| Terate ® HT 5349 | 40.01 | 54.66 | 54.66 | 54.66 | 54.66 | 57.98 | 47.87 | 47.87 |
| Voranol ® 280 | — | — | — | — | — | — | 10.00 | 15.00 |
| Voranol ® 370 | 2.00 | 2.15 | 2.15 | 2.15 | 2.15 | 2.46 | 2.46 | 2.46 |
| Carpol ® GSP-280 | 16.00 | 22.59 | 22.59 | 22.59 | 22.59 | 16.43 | — | — |
| Carpol ® GP-5015 | 20.00 | — | — | — | — | — | — | — |
| Carpol ® GP-700 | — | — | — | — | — | — | 14.52 | — |
| Vorasurf ® 504 | — | — | — | — | — | — | — | 9.52 |
| Dabco ® DC193 | 2.00 | 2.00 | 2.00 | 2.00 | 2.00 | 2.00 | 2.00 | 2.00 |
| Dabco ® T-120 | 0.25 | 0.25 | 0.25 | 0.25 | 0.25 | 0.25 | 0.25 | 0.25 |
| Dabco ® K-15 | 0.25 | 0.25 | 0.25 | 0.25 | 0.25 | 0.25 | 0.25 | 0.25 |
| Polycat ® 204 | 4.00 | 4.00 | 4.00 | 4.00 | 4.00 | 4.00 | 4.00 | 4.00 |
| Water | 1.49 | 1.43 | 1.43 | 1.43 | 1.43 | 1.26 | 1.25 | 1.25 |
| Opteon ™ 1100 | 6.00 | 6.69 | 6.69 | 6.69 | 6.69 | 8.00 | 8.00 | 8.00 |
| Process | | | | | | | | |
| A:B vol. ratio | 1:1 | 1:1 | 1:1 | 1:1 | 1:1 | 1:1 | 1:1 | 1:1 |
| Isocyanate Index | 1.149 | 0.991 | 0.991 | 0.991 | 0.991 | 1.007 | 1.058 | 1.119 |

*Comparative run.

TABLE 13B

| Example 22-Run | 17 | 18 | 19 | 20 | 21 | 22 | 23 |
|---|---|---|---|---|---|---|---|
| B side | | | | | | | |
| Viscosity (cPs; at 25° C.) | 695 | 470 | | 890 | 1200 | 1955 | 1285 |
| DBAA | 9.85 | 12.31 | 12.42 | 12.43 | 12.47 | 12.86 | 12.90 |
| Terate ® HT 5349 | 47.87 | 47.87 | 48.72 | 41.01 | 56.81 | 59.66 | 58.38 |
| Voranol ® 280 | | 10.00 | 2.46 | 2.48 | 2.49 | 2.49 | 2.57 |
| Voranol ® 370 | 12.46 | | | | | | |
| Carpol ® GSP-280 | | | | 29.26 | 16.43 | 16.43 | 16.43 |
| Carpol ® GP-1500 | 14.52 | 14.52 | 24.74 | | | | |
| Dabco ® DC193 | 2.00 | 2.00 | 2.00 | 2.00 | 2.00 | 2.00 | 2.00 |
| Dabco ® T-120 | 0.25 | 0.25 | 0.25 | 0.25 | 0.25 | 0.25 | 0.25 |
| Dabco ® K-15 | 0.25 | 0.25 | 0.25 | 0.25 | 0.25 | 0.25 | 0.25 |
| Polycat ® 204 | 4.00 | 4.00 | 4.00 | 4.00 | 4.00 | 4.00 | 4.00 |
| Water | 1.25 | 1.25 | 1.50 | 0.85 | 1.15 | 1.52 | 1.38 |
| Opteon ™ 1100 | 8.00 | 8.00 | 6.00 | 12.00 | 9.00 | 5.77 | 7.00 |
| Process | | | | | | | |
| A:B vol. ratio | 1:1 | 1:1 | 1:1 | 1:1 | 1:1 | 1:1 | 1:1 |
| Isocyanate Index | 1.075 | 1.111 | 1.097 | 1.122 | 1.028 | 0.957 | 0.982 |

TABLE 13B-continued

| Example 22-Run | 24 | 25 | 26 | 27 | 28 | 29 | 30 |
|---|---|---|---|---|---|---|---|
| B side | | | | | | | |
| Viscosity (cPs; at 25° C.) | 1395 | 2220 | 2420 | 2240 | 890 | 1010 | 1570 |
| DBAA | 13.44 | 13.44 | 13.54 | 15.28 | 16.11 | 17.23 | 20.57 |
| Terate ® HT 5349 | 58.84 | 61.34 | 64.74 | 49.47 | 36.64 | 49.21 | 55.50 |
| Voranol ® 280 | 2.58 | 2.69 | 2.69 | 2.71 | 3.06 | 3.22 | 3.45 |
| Voranol ® 370 | | | | | | | |
| Carpol ® GSP-280 | 16.43 | 16.43 | 16.43 | 29.95 | 29.95 | 17.00 | 16.43 |
| Carpol ® GP-1500 | | | | | | | |
| Dabco ® DC193 | 2.00 | 2.00 | 2.00 | 2.00 | 2.00 | 2.00 | 2.00 |
| Dabco ® T-120 | 0.25 | 0.25 | 0.25 | 0.25 | 0.25 | 0.25 | 0.25 |
| Dabco ® K-15 | 0.25 | 0.25 | 0.25 | 0.25 | 0.25 | 0.25 | 0.25 |
| Polycat ® 204 | 4.00 | 4.00 | 4.00 | 4.00 | 4.00 | 4.00 | 4.00 |
| Water | 1.48 | 1.78 | 2.17 | 2.19 | 0.81 | 0.87 | 1.88 |
| Opteon ™ 1100 | 6.00 | 3.50 | 0.00 | 0.00 | 12.00 | 11.26 | 2.21 |
| Process | | | | | | | |
| A:B vol. ratio | 1:1 | 1:1 | 1:1 | 1:1 | 1:1 | 1:1 | 1:1 |
| Isocyanate Index | 0.963 | 0.913 | 0.856 | 0.868 | 1.12 | 1.074 | 0.877 |

TABLE 13C

| Example 22-Run | 31 | 32 | 33 | 34 | 35 | 36 | 37 |
|---|---|---|---|---|---|---|---|
| B side | | | | | | | |
| Viscosity (cPs; at 25° C.) | 600 | 1570 | 1630 | 1115 | 1035 | 575 | 650 |
| DBAA | 16.75 | 20.00 | 20.00 | 20.00 | 20.00 | 20.00 | 17.16 |
| Terate ® HT 5349 | 35.51 | 47.10 | 47.10 | 35.51 | 35.51 | 41.28 | 43.05 |
| Voranol ® 370 | 4.19 | 5.00 | 5.00 | 5.00 | 5.00 | 5.00 | — |
| Carpol ® GSP-280 | 26.25 | 22.60 | 22.60 | 29.95 | 29.95 | 16.43 | 21.47 |
| Dabco ® DC193 | 2.00 | 2.00 | 2.00 | 2.00 | 2.00 | 2.00 | 2.00 |
| Dabco ® T-120 | 0.25 | 0.25 | 0.25 | 0.25 | 0.25 | 0.25 | 0.25 |
| Dabco ® K-15 | 0.25 | 0.25 | 0.25 | 0.25 | 0.25 | 0.25 | 0.25 |
| Polycat ® 204 | 4.00 | 4.00 | 4.00 | 4.00 | 4.00 | 4.00 | 4.00 |
| Water | 0.78 | 2.12 | 2.13 | 1.66 | 1.65 | 0.74 | 0.73 |
| Opteon ™ 1100 | 12.00 | 0.00 | 0.00 | 4.24 | 4.24 | 12.00 | 12.00 |
| Process | | | | | | | |
| A:B vol. ratio | 1:1 | 1:1 | 1:1 | 1:1 | 1:1 | 1:1 | 1:1 |
| Isocyanate Index | 1.103 | 0.840 | 0.840 | 0.921 | 0.922 | 1.076 | 1.100 |

TABLE 14A

| Example 22-Run | 1* | 2* | 3 | 4 | 5 | 6 | 7 |
|---|---|---|---|---|---|---|---|
| Density, lb/ft$^3$ | 2.17 | 2.18 | 2.10 | 1.98 | 2.13 | 1.99 | 2.19 |
| Density, kg/m$^3$ | 34.8 | 34.9 | 33.6 | 31.7 | 34.1 | 31.9 | 35.1 |
| Dimensional stability$^1$ (vol. change) | −66.50 | 0.14 | −0.32 | 3.21 | −56.61 | 1.21 | 1.37 |
| Compressive Strength, psi | 19.4 | 24.8 | 24.7 | 22.3 | 18.1 | 27.2 | 17.7 |
| Compressive Strength, kPa | 133.8 | 171.0 | 170.3 | 153.8 | 124.8 | 187.5 | 122.0 |
| R-value, /in. | 6.33 | 7.68 | 7.95 | 7.11 | 6.76 | 4.93 | 4.62 |
| R-value, m$^2$K/W | 1.115 | 1.353 | 1.400 | 1.252 | 1.191 | 0.868 | 8.41 |
| Peak Heat Release Rate | 280 | 275 | 241 | 233 | 227 | 235 | 656 |
| Predicted Flame Spread Index | 26.0 | 23.7 | 23.7 | 22.9 | 22.1 | 21.4 | 21.6 |
| Predicted Smoke Index | 43 | 109 | 35 | 13 | 19 | 64 | 1060 |

TABLE 14A-continued

| Example 22-Run | 8 | 9 | 10 | 11 | 12 | 13 | 14 |
|---|---|---|---|---|---|---|---|
| Density, lb/ft$^3$ | 1.95 | 1.91 | 1.85 | 1.90 | 1.84 | 1.92 | 1.88 |
| Density, kg/m$^3$ | 31.2 | 30.6 | 29.6 | 30.4 | 29.5 | 30.8 | 30.1 |
| Dimensional stability$^1$ (vol. change) | 1.99 | −0.74 | 0.03 | −1.30 | −0.44 | −0.20 | 1.25 |
| Compressive Strength, psi | 16.1 | 15.0 | 24.1 | 24.3 | 23.7 | 23.5 | 22.2 |
| Compressive Strength, kPa | 111.0 | 103.4 | 166.2 | 167.5 | 163.4 | 162.0 | 153.1 |
| R-value, /in. | 4.86 | 5.64 | 4.56 | 4.79 | 4.93 | 4.93 | 4.63 |
| R-value, m$^2$K/W | 0.856 | 0.993 | 0.803 | 0.844 | 0.868 | 0.868 | 0.815 |
| Peak Heat Release Rate | 507 | 435 | 215 | 199 | 225 | 219 | 208 |
| Predicted Flame Spread Index | 22.2 | 22.2 | 18.9 | 19.9 | 18.9 | 20.0 | 20.0 |
| Predicted Smoke Index | 629 | 781 | 57 | 34 | 47 | 37 | 48 |

*Comparative run.
$^1$Dimensional stability was measured at 70° C. for 14 days at 95% RH.

TABLE 14B

| Example 22-Run | 15 | 16 | 17 | 18 | 19 | 20 | 21 |
|---|---|---|---|---|---|---|---|
| Density, lb/ft$^3$ | 1.93 | 1.97 | 1.94 | 1.93 | 1.87 | 1.81 | 1.97 |
| Density, kg/m$^3$ | 30.9 | 31.6 | 31.1 | 30.9 | 30.0 | 29.0 | 31.6 |
| Dimensional stability$^1$ (vol. change) | 9.36 | −11.57 | −27.1 | −35.73 | — | −4.72 | 2.01 |
| Compressive Strength, psi | 21.9 | 11.1 | 11.2 | 11.4 | 7.5 | 18.3 | 26.3 |
| Compressive Strength, kPa | 151.0 | 76.5 | 77.2 | 78.6 | 51.7 | 126.2 | 181.3 |
| R-value, /in. | 6.37 | 6.70 | 6.92 | 7.06 | 6.40 | 7.73 | 4.76 |
| R-value, m$^2$K/W | 1.122 | 1.18 | 1.219 | 1.243 | 1.127 | 1.361 | 0.838 |
| Peak Heat Release Rate | 220 | 518 | 431 | 404 | 479 | 222 | 219 |
| Predicted Flame Spread Index | 21.3 | 21.9 | 19.9 | 21.6 | 22.5 | 19.9 | 20.6 |
| Predicted Smoke Index | 35 | 1003 | 1055 | 906 | 479 | 26 | 36 |

| Example 22-Run | 22 | 23 | 24 | 25 | 26 | 27 |
|---|---|---|---|---|---|---|
| Density, lb/ft$^3$ | 1.95 | 1.93 | 1.91 | 1.93 | 2.19 | 2.08 |
| Density, kg/m$^3$ | 31.2 | 30.9 | 30.6 | 30.9 | 35.1 | 33.3 |
| Dimensional stability$^1$ (vol. change) | −41.59 | −0.68 | 1.32 | −57.31 | −62.93 | −47.63 |
| Compressive Strength, psi | 15.4 | 23.4 | 23.0 | 12.6 | 13.6 | 12.9 |
| Compressive Strength, kPa | 106.2 | 161.3 | 158.6 | 86.9 | 93.8 | 88.9 |
| R-value, /in. | 7.04 | 4.81 | 4.81 | 7.01 | 6.24 | 6.58 |
| R-value, m$^2$K/W | 1.24 | 0.847 | 0.847 | 1.235 | 1.099 | 1.159 |
| Peak Heat Release Rate | 221 | 233 | 236 | 214 | 201 | 219 |
| Predicted Flame Spread Index | 20.2 | 21.0 | 20.3 | 21.6 | 22.4 | 21.5 |
| Predicted Smoke Index | 48 | 44 | 61 | 56 | 28 | 116 |

$^1$Dimensional stability was measured at 70° C. for 14 days at 95% RH.

TABLE 14C

| Example 22-Run | 28 | 29 | 30 | 31 | 32 | 33 | 34 | 35 | 36 | 37 |
|---|---|---|---|---|---|---|---|---|---|---|
| Density, lb/ft$^3$ | 1.82 | 1.96 | 1.90 | 1.83 | 1.93 | 2.17 | 1.99 | 1.88 | 1.67 | 1.85 |
| Density, kg/m$^3$ | 29.1 | 31.4 | 30.4 | 29.3 | 30.9 | 34.8 | 31.9 | 30.1 | 26.8 | 29.6 |
| Dimensional stability$^1$ (vol. change) | 1.18 | −2.71 | −1.04 | −16.55 | −47.57 | −80.89 | −39.23 | −57.00 | −23.00 | −17.5 |

TABLE 14C-continued

| Compressive Strength, psi | 16.5 | 16.7 | 22.2 | 15.6 | 10.0 | 14.5 | 11.5 | 12.6 | 13.3 | 14.6 |
|---|---|---|---|---|---|---|---|---|---|---|
| Compressive Strength, kPa | 113.8 | 115.1 | 153.1 | 107.6 | 68.9 | 100.0 | 79.3 | 86.9 | 91.7 | 100.7 |
| R-value, /in. | 7.67 | 7.24 | 4.97 | 7.66 | 5.69 | 6.89 | 6.97 | 7.01 | 7.85 | 7.21 |
| R-value, $m^2K/W$ | 1.351 | 1.275 | 0.875 | 1.349 | 1.002 | 1.213 | 1.227 | 1.235 | 1.382 | 1.270 |
| Peak Heat Release Rate | 192 | 200 | 204 | 193 | 190 | 213 | 197 | 207 | 187 | 172 |
| Predicted Flame Spread Index | 20.3 | 19.0 | 16.9 | 18.1 | 17.7 | 18.3 | 17.6 | 18.2 | 16.8 | 18.1 |
| Predicted Smoke Index | 51 | 40 | 54 | 48 | 39 | 56 | 79 | 95 | 41 | 43 |

[1]Dimensional stability was measured at 70° C. for 14 days at 95% RH.

Components referred to by chemical name or formula anywhere in the specification or claims hereof, whether referred to in the singular or plural, are identified as they exist prior to coming into contact with another substance referred to by chemical name or chemical type (e.g., another component, a solvent, or etc.). It matters not what chemical changes, transformations and/or reactions, if any, take place in the resulting mixture or solution as such changes, transformations, and/or reactions are the natural result of bringing the specified components together under the conditions called for pursuant to this disclosure. Thus the components are identified as ingredients to be brought together in connection with performing a desired operation or in forming a desired composition. Also, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. The fact that a substance, component or ingredient may have lost its original identity through a chemical reaction or transformation during the course of contacting, blending or mixing operations, if conducted in accordance with this disclosure and with ordinary skill of a chemist, is thus of no practical concern.

The invention described and claimed herein is not to be limited in scope by the specific examples and embodiments herein disclosed, since these examples and embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fail within the scope of the appended claims.

That which is claimed is:

1. A formulation comprising 2,3-dibromoallyl alcohol, at least one polyol, at least one catalyst, and at least one surfactant.

2. A formulation as in claim 1 wherein the polyol is a polyether polyol and/or a polyester polyol.

3. A formulation as in claim 1 wherein the amount of 2,3-dibromoallyl alcohol is about 1 wt % to about 25 wt %, the amount of polyol is about 40 wt % to about 80 wt %, the amount of surfactant is about 0.1 wt % to about 5 wt %, and/or the amount of catalyst is about 0.25 wt % to about 10 wt %, based on the total weight of the formulation.

4. A formulation as in claim 1 wherein the polyol has a functionality of about 3 to about 7.

5. A formulation as in claim 3 further comprising a blowing agent in the amount of about 0.5 wt % to about 20 wt %.

6. A polyurethane formed from components comprising at least one polyisocyanate and a formulation as in any of claims 1-5.

7. A process for forming a polyurethane, which process comprises
contacting A) at least one isocyanate and/or polyisocyanate and B) a formulation formed from 2,3-dibromoallyl alcohol, at least one polyol, at least one catalyst, and at least one surfactant, to form a mixture; and
allowing the mixture to cure to form a polyurethane.

8. A process as in claim 7 wherein B) further comprises at least one blowing agent.

9. A process as in claim 8 wherein A) and B) are in amounts such that the Isocyanate Index is about 80 to about 200, and wherein a flexible polyurethane foam is formed.

10. A process as in claim 7 wherein A) and B) are in amounts such that the Isocyanate Index is about 85 to about 1000, and wherein a rigid polyurethane foam is formed.

11. A polyurethane formed as in any of claims 7-10.

12. A polyurethane formed from ingredients comprising 2,3-dibromoallyl alcohol, at least one polyol, at least one catalyst, at least one surfactant, and at least one polyisocyanate.

13. A polyurethane as in claim 12 wherein the polyol is an aromatic polyester polyol and either a polyether polyol or at least one sucrose/glycerine polyol; wherein the catalyst is potassium octoate and/or dibutylbis(dodecylthio) stannane; wherein the surfactant is a silicone glycol; and/or wherein the polyisocyanate is diphenylmethane diisocyanate.

14. A polyurethane as in claim 13 wherein the ingredients further comprise a blowing agent selected from water, trans-1-chloro-3,3,3-trifluoropropene, 1,2-bis(trifluoromethyl)ethene or a mixture of any two or more of these.

15. A polyurethane as in claim 13 wherein the amount of 2,3-dibromoallyl alcohol is about 1.5 wt % to about 10 wt %; wherein the amount of polyol is about 25 wt % to about 35 wt %; wherein the amount of catalyst is about 0.5 wt % to about 4 wt %; and/or wherein the amount of surfactant is about 0.25 wt % to about 2.5 wt %, based on the total weight of the polyurethane.

16. A polyurethane as in claim 13 wherein the aromatic polyester polyol has a functionality of about 1.75 to about 2.75 and a hydroxyl number in the range of about 200 to about 350.

* * * * *